(12) United States Patent
Gai et al.

(10) Patent No.: US 10,975,020 B2
(45) Date of Patent: Apr. 13, 2021

(54) PROCESS FOR QUENCHING A GASEOUS REACTION MIXTURE OBTAINED IN THE GAS PHASE PHOSGENATION OF DIAMINES

(71) Applicant: Covestro Deutschland AG, Leverkusen (DE)

(72) Inventors: Yuguo Gai, Shanghai (CN); Zhangyong Ming, Shanghai (CN); Qiang Wei, Shanghai (CN); Joachim Zechlin, Neuss (DE); Thomas Bludowsky, Ratingen (DE); Wolfgang Taube, Neuss (DE); Volker Michele, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/641,697

(22) PCT Filed: Sep. 7, 2018

(86) PCT No.: PCT/EP2018/074209
§ 371 (c)(1),
(2) Date: Feb. 25, 2020

(87) PCT Pub. No.: WO2019/048644
PCT Pub. Date: Mar. 14, 2019

(65) Prior Publication Data
US 2020/0361857 A1    Nov. 19, 2020

(30) Foreign Application Priority Data

Sep. 11, 2017 (CN) .......................... 201710811156.1
Nov. 16, 2017 (EP) ..................................... 17202133

(51) Int. Cl.
C07C 263/10    (2006.01)
C07C 263/20    (2006.01)
C07C 265/14    (2006.01)

(52) U.S. Cl.
CPC .......... *C07C 263/10* (2013.01); *C07C 263/20* (2013.01); *C07C 265/14* (2013.01)

(58) Field of Classification Search
CPC .... C07C 263/10; C07C 263/20; C07C 265/14
See application file for complete search history.

(56) References Cited

U.S. PATENT DOCUMENTS

| | | | |
|---|---|---|---|
| 4,847,408 A | 7/1989 | Frosch et al. | |
| 6,800,781 B2 * | 10/2004 | Herold | C07C 263/10 560/347 |
| 7,615,662 B2 | 11/2009 | Pohl et al. | |
| 8,759,568 B2 * | 6/2014 | Lehr | C07C 263/20 560/347 |
| 9,376,377 B2 * | 6/2016 | Steffens | C07C 263/10 |
| 2012/0004445 A1 | 1/2012 | Lehr et al. | |

OTHER PUBLICATIONS

International Search Report, PCT/EP2018/074209, dated Nov. 28, 2018, Authorized officer: J. Matés Valdivielso.

\* cited by examiner

*Primary Examiner* — Paul A Zucker
(74) *Attorney, Agent, or Firm* — Donald R. Palladino

(57) ABSTRACT

A process for quenching, in a quenching zone, a gaseous reaction mixture that includes a diisocyanate, phosgene and hydrogen chloride that is obtained in a reaction zone upstream of the quenching zone by phosgenation of a diamine in the gas phase. The process includes injecting a deposit preventing liquid in a deposit preventing zone located between the reaction zone and the quenching zone by passing the deposit preventing liquid through spray nozzles for the deposit preventing liquid at the entrance to the deposit preventing zone. Each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, and/or (ii) to areas in a cross-sectional plane of the deposit preventing zone before the entrance to the quenching zone.

15 Claims, 2 Drawing Sheets

PROCESS FOR QUENCHING A GASEOUS REACTION MIXTURE OBTAINED IN THE GAS PHASE PHOSGENATION OF DIAMINES

CROSS-REFERENCE TO RELATED APPLICATION

This application is a national stage application under 35 U.S.C. § 371 of PCT/EP2018/074209, filed Sep. 7, 2018, which claims the benefit of European Application No. 17202133.9, filed Nov. 16, 2017 and CN201710811156.1, filed Sep. 11, 2017, each of which is incorporated herein by reference.

FIELD OF THE INVENTION

The present invention belongs to the field of polyurethanes. More particularly, the present invention belongs to the field of isocyanates which are, alongside isocyanate-reactive compounds such as, for example, polyether polyols, one of the two major components in polyurethane production. In particular, the present invention relates to a process for quenching a gaseous reaction mixture that is obtained in a gas phase phosgenation of diamines to yield the corresponding diisocyanates. The present invention also relates to a process for producing diisocyanates by phosgenation of the corresponding diamines.

BACKGROUND OF THE INVENTION

The preparation of isocyanates by phosgenating the corresponding amines can in principle be effected by a liquid phase or gas phase phosgenation. Gas phase phosgenation is notable in that a higher selectivity, a lower holdup of toxic phosgene and a reduced amount of energy are required.

The preparation of diisocyanates by reacting diamines with phosgene in the gas phase is described, for example, in EP 0 289 840 A1. The amine and the phosgene react with release of hydrogen chloride (HCl) to give the corresponding isocyanates. The diisocyanates formed in a cylindrical reaction chamber, such as a tubular reactor, are not thermally stable at the reaction temperatures of 300 to 500° C. Rapid cooling of the reaction gases after the phosgenation reaction to temperatures below 200° C. is therefore needed to avoid the formation of undesired secondary products due to the thermal decomposition of diisocyanate or by further reaction. For this purpose, in EP 0 289 840 A1, the gaseous mixture continually leaving the reaction chamber, which contains, inter alia, diisocyanate, phosgene and hydrogen chloride, is passed into an inert solvent, e.g. dichlorobenzene. The disadvantage of this process is that the rate of flow at which the gas mixture is passed through the solvent bath has to be relatively low because at too high rates of flow the solvent and the compounds dissolved therein would be carried over. In a subsequent step, the liquid compounds have to be separated from the gas. Another disadvantage is that, due to the low rates of flow and a small heat transfer term, large solvent containers have to be used to produce the cooling effect.

Furthermore, processes are known which use heat exchangers and/or expand the gases into a vacuum to cool the reaction gases. The disadvantage of heat exchangers is that, due to poor heat transfer, large exchange surfaces and thus large heat exchangers are required for effective cooling. In addition, deposits of solids on the relatively cold surfaces of the heat exchangers takes place due to secondary reactions of the gas mixture on these surfaces, such as e.g. decomposition or polymerization. The transfer of heat is further impaired by these deposits and this leads to a higher residence time and thus results in a further increase in secondary product formation. On top of that, undesired shutdown times are produced for the entire plant due to cleaning of the cooling stage.

U.S. Pat. No. 6,800,781 B2 (also published as U.S. 2004/0068137 A1) discloses a process for quenching a gaseous reaction mixture during the phosgenation of diamines in the gas phase to produce diisocyanates, by injecting a quenching liquid into the gas mixture continuously flowing out of a cylindrical reaction zone into the downstream cylindrical quenching zone, wherein the quenching liquid is injected with the aid of at least two spray nozzles arranged at the entrance to the quenching zone at equal distances along the circumference of the quenching zone. The disadvantage of such a process is that there are solid deposits above the nozzles for injecting the quenching liquid after operation for a period of time (for example several weeks). The solid deposits horizontally grow, finally blocking the passage of the gaseous reaction mixture, meanwhile the growing solid deposits lead to high differential pressure in the gas phase over the reactor. As a consequence, the reactor has to be shut down after operation for a period of time (for example several weeks) because the whole reactor needs to be hydroblasted to remove the solid deposits above the quench zone, resulting in decrease of productivity.

U.S. Pat. No. 7,615,662 B2 (also published as U.S. 2008/167490 A1) relates to a process for the preparation of isocyanates by reaction of corresponding primary amine(s) with phosgene in the gas phase. In this process, the reaction is terminated by guiding the reaction mixture out of the reaction chamber through a cooling stretch into which liquids are injected. Direct cooling takes place in the cooling stretch in one stage in two or more cooling zones connected in series.

U.S. 2012/0004445 A1 is concerned with a process for preparing isocyanates by reacting the corresponding amines with phosgene in the gas phase, in which undesired reactions and the formation of solid deposits are prevented or at least greatly reduced. The hot gaseous reaction gas mixture obtained in the phosgenation step is cooled in a quench step by adding, in a quenching zone, a liquid medium to form a mixture of reaction gas and quench medium as the product stream, which process is carried out such that the walls of the quenching zone are essentially completely wetted with a liquid. The application does not teach to wet the walls above the quenching zone, i.e. before entrance to the quenching zone.

Thus there is a need for an improved quenching process to avoid the formation of solid deposits above the quenching zone and/or remove the solid deposits formed above the quenching zone.

SUMMARY OF THE INVENTION

The technical problem to be solved by the present invention is to provide a quenching process to avoid the formation of solid deposits above the quenching zone and/or remove the solid deposits formed above the quenching zone.

In its broadest sense, the present invention therefore provides a process for quenching, in a quenching zone, a gaseous reaction mixture comprising a diisocyanate, phosgene and hydrogen chloride that is obtained in a reaction zone upstream of the quenching zone by phosgenation of a diamine in the gas phase, the process comprising:

(a) injecting a quenching liquid in the quenching zone by passing the quenching liquid through spray nozzles for the quenching liquid arranged at the entrance to the quenching zone, thereby partially condensing the gaseous reaction mixture; and (b) injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, and/or (ii) to areas in a cross-sectional plane of the deposit preventing zone before the entrance to the quenching zone.

In another aspect, the present invention provides a process for preparing a diisocyanate by phosgenation of a diamine (i.e. the diamine corresponding to the diisocyanate) in the gas phase, wherein the process for quenching as described above is used to quench, i.e. to cool and partially condense, the gaseous reaction mixture comprising a diisocyanate, phosgene and hydrogen chloride.

The "entrance to the deposit preventing zone" and the "entrance to the quenching zone" are defined by the location of the respective spray nozzles in the direction of flow of the reaction gas. If several spray nozzles are arranged alongside the direction of flow of the reaction gas in one of these zones (as described for the quenching zone in U.S. Pat. No. 7,615,662 B2), the first spray nozzle in the direction of flow of the reaction gas defines the entrance to the respective zone.

As will be explained in more detail below, spraying the deposit preventing liquid "(i) onto a wall segment of the deposit preventing zone that is adjacent to said spray nozzle for the deposit preventing liquid to produce a film of the deposit preventing liquid flowing along the wall" means that the deposit preventing liquid emerging from a certain nozzle does not wet (or does at least not essentially wet) the area of the wall opposite to said nozzle but only (or at least essentially only) the area below (underneath) said nozzle, as shown in FIG. 1.

As will also be explained in more detail below, spraying the deposit preventing liquid "(ii) to areas in a cross-sectional plane of the deposit preventing zone before the entrance to the quenching zone" serves the purpose of breaking loose solid deposits. In this embodiment, the "deposit preventing liquid" actually acts as a "deposit breaking liquid". For reasons of linguistic simplification, however, the term "deposit preventing liquid" is used throughout the text, regardless which variant is referred to.

The term "quenching liquid" as used in the context of this invention is well-known in the art and refers to any kind of liquid that does not react (or that does at least not substantially react) with the product diisocyanate and the boiling point of which is such that it is partly vaporised upon contact with the hot gaseous reaction mixture, thereby providing efficient and rapid cooling of the latter. Examples of suitable quenching liquids are, as will be explained in greater detail below, organic solvents, the product diisocyanate and mixtures of these.

The term "deposit preventing liquid" as used in the context of this invention refers to any kind of liquid that does not react (or that does at least not substantially react) with the product diisocyanate. Preferably, as will be explained in greater detail below, the deposit preventing liquid can be the same kind of liquid (i.e. can have the same chemical composition) as the quenching liquid; if a mixture of an organic solvent and the product isocyanate is used, the concentration of the product diisocyanate in the solution may, however, differ. The deposit preventing liquid used in variant b)(i) can be the same as that used in variant b)(ii).

BRIEF DESCRIPTION OF THE FIGURES

The present invention will be described for purposes of illustration in conjunction with the figures, wherein.

1: deposit preventing zone, 2: pipe, 3: nozzle head, 4: spray nozzles for the quenching liquid, 5: quenching zone, 6: liquid collection container acting simultaneously as a pump reservoir and as apparatus to separate gas and liquid, 7: spray nozzles for the deposit preventing liquid, 8: the direction of flow of the quenching liquid, 9: the direction of flow of the gaseous reaction mixture, 10: film of deposit preventing liquid, 11: wall of the quenching zone, 12: entrance to the quenching zone, 13: wall of the deposit preventing zone, 14: entrance to the deposit preventing zone, 15: reaction zone.

Figure 2:
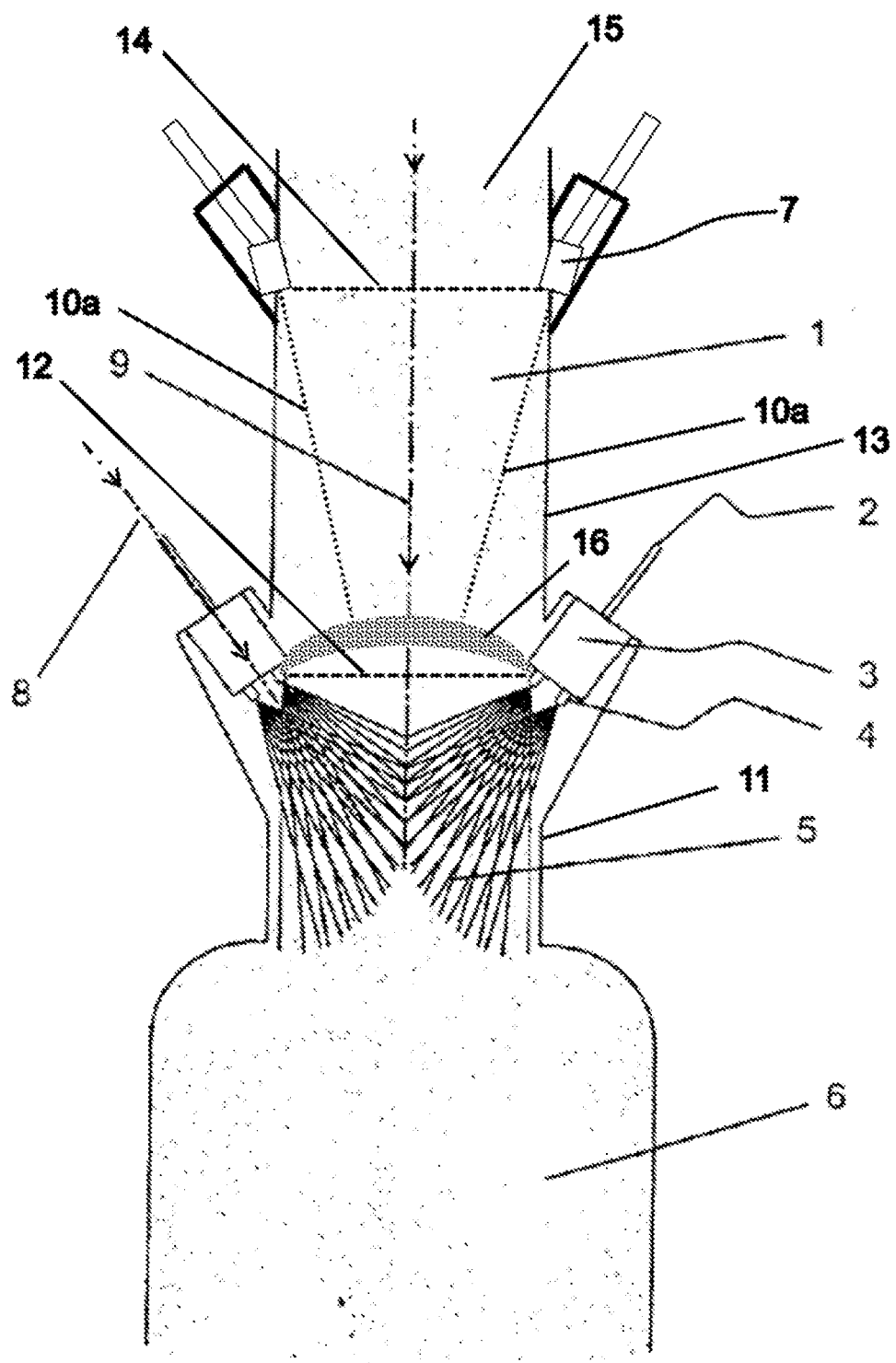

FIG. 2 shows a schematic diagram of another embodiment according to the present invention, wherein the process is conducted according to variant b)(ii). The reference numerals have the following meanings:

1: deposit preventing zone, 2: pipe, 3: nozzle head, 4: spray nozzles for the quenching liquid, 5: quenching zone, 6: liquid collection container acting simultaneously as a pump reservoir and as apparatus to separate gas and liquid, 7: spray nozzles for the deposit preventing liquid, 8: the direction of flow of the quenching liquid, 9: the direction of flow of the gaseous reaction mixture, 10a: deposit preventing liquid stream (acting in this embodiment as deposit breaking liquid stream), 11: wall of the quenching zone, 12: entrance to the quenching zone, 13: wall of the deposit preventing zone, 14: entrance to the deposit preventing zone, 15: reaction zone, 16: solid deposits (typically porous).

DETAILED DESCRIPTION OF THE INVENTION

The present invention is now described for purposes of illustration and not limitation.

The present invention provides a process for quenching, in a quenching zone, a gaseous reaction mixture comprising a diisocyanate, phosgene and hydrogen chloride that is obtained in a reaction zone upstream of the quenching zone by phosgenation of a diamine in the gas phase, the process comprising:

(a) injecting a quenching liquid in the quenching zone by passing the quenching liquid through spray nozzles for the quenching liquid arranged at the entrance to the quenching zone, thereby partially condensing the gaseous reaction mixture; and (b) injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, and/or (ii) to areas in a cross-sectional plane of the deposit preventing zone before the entrance to the quenching zone.

In addition to phosgene, hydrogen chloride and the major product, the diisocyanate corresponding to the reactant diamine, the gaseous reaction mixture may also contain further isocyanates produced as secondary products (for example oligomers of the product diisocyanate), other secondary products as well as an inert gas such as nitrogen and/or an organic solvent(s).

Examples of diisocyanates that can be prepared by gas phase phosgenation of diamines include, but are not limited to, hexamethylene diisocyanate (HDI), isophorone diisocyanate (IPDI), naphthylene diisocyanate (NDI), toluene diisocyanate (TDI), xylylene diisocyanate (XDI), dipenylmethane diisocyanate and dicyclohexylmethane diisocyanate (HMDI). The process for quenching according to the invention can be used in the production of all of these diisocyanates.

The reaction zone, the deposit preventing zone and the quenching zone are preferably arranged in a single apparatus, i.e. a reactor for producing diisocyanates by gas phase phosgenation of diamines.

The reaction zone is preferably cylindrical. The reaction zone is the area where the phosgenation reaction of diamine and phosgene occurs in the reactor. The phosgenation of diamine is completed at the exit of the reaction zone (i.e. at the entrance to the deposit preventing zone).

The quenching zone is the area where the gaseous reaction mixture is partly condensed by injection of the quenching liquid into the stream of the gaseous reaction mixture. The quenching zone is preferably cylindrical.

In the present application, the deposit preventing zone refers to the area between the exit of the reaction zone and the entrance of the quenching zone. The height of the deposit preventing zone is preferably from 1.5 cm to 5 m, more preferably 20 cm to 4 m, even more preferably 50 cm to 3 m, most preferably 80 cm to 2.5 m. The deposit preventing zone is, just as the reaction zone and the quenching zone, preferably cylindrical. In that case, generally, the diameter of the deposit preventing zone is the same as that of the reaction zone.

The reaction zone and the quenching zone are joined via the deposit preventing zone. In the terminology of the present invention, each zone is named based on the different unit processes occurring therein, for example, gas phase reaction (=reaction zone), wetting and protecting the wall (=deposit preventing zone) as well as direct contact heat exchange (quenching) between a gas and a liquid (=quenching zone).

The spray nozzles for the deposit preventing liquid are preferably arranged at equal distances along the circumference of the entrance of the deposit preventing zone in all embodiments.

The number of spray nozzles for injecting the deposit preventing liquid onto a wall of the deposit preventing zone that is adjacent to the respective nozzle (b)(i)) is not less than two. The person skilled in the art can determine the number of spray nozzles for injecting the deposit preventing liquid onto the wall of the deposit preventing zone, such as to fully cover the wall with liquid, based on the circumference of the deposit preventing zone and the chosen nozzles' installation position and spray angle, for example, 2-16, preferably, 4-12.

The number of spray nozzles for injecting the deposit preventing liquid to areas in the cross-sectional plane of the deposit preventing zone before the entrance to the quenching zone (b)(ii)) is not less than two. The person skilled in the art can determine the number of spray nozzles for injecting the deposit preventing liquid to areas in the cross-sectional plane of the deposit preventing zone before the entrance to the quenching zone based on the diameter of the deposit preventing zone, for example, 2-16, preferably, 4-12.

In an embodiment according to the present invention, the spray nozzles for the deposit preventing liquid include only spray nozzles for injecting the deposit preventing liquid onto the wall of the deposit preventing zone. In this embodiment, therefore, the process of the invention is carried out in accordance with variant b)(i) only.

In another embodiment according to the present invention, the spray nozzles for the deposit preventing liquid include only spray nozzles for injecting the deposit preventing liquid to areas in the cross-sectional plane of the deposit preventing zone before the entrance to the quenching zone. In this embodiment, therefore, the process of the invention is carried out in accordance with variant b)(ii) only.

The deposit preventing liquid comprises an organic solvent or a mixture of different organic solvents which do not react with the diisocyanate formed. Suitable solvents can be selected from, for example, toluene, chlorobenzene, chlorotoluene, dichlorobenzene, xylene and chloronaphthalene. Dichlorobenzene includes para-dichlorobenzene and ortho-dichlorobenzene, and xylene includes para-xylene and ortho-xylene.

A solution of the diisocyanate formed in one of above organic solvents may also be used. In this case, the proportion of solvent is preferably 40% to 99% by mass, preferably 80% to 95% by mass, based on the total mass of the solution.

The deposit preventing liquid can also be a mixture of the solvent(s) mentioned above, the diisocyanate formed and phosgene. In this case, the proportion of the solvent is preferably 40 to 99% by mass, preferably 80-95% by mass, based on the total mass of the solution.

The temperature of the deposit preventing liquid is from −20° C. to 200° C. Preferably, the temperature of the deposit preventing liquid is from 100° C. to 180° C.

Preferably, the pressure of the deposit preventing liquid injected to areas in the cross-sectional plane of the deposit preventing zone before the entrance to the quenching zone in embodiment (ii) is 5 barg to 1000 barg, preferably 50 barg to 500 barg.

The deposit preventing liquid injected onto the wall of the deposit preventing zone (i.e. in accordance with b)(i)) is not atomized, substantially flows downwards along the wall of the deposit preventing zone to form a film of the deposit preventing liquid on the wall of the deposit preventing zone, and only a very small portion of solvent vaporizes due to heat transferred from the hot gaseous reaction mixture. "Not atomized" in this context means that the formation of very fine droplets (such as droplets having a diameter of up to 100 µm) is avoided largely to completely. The deposit preventing liquid is injected such that a liquid film forms, which film flows down the wall adjacent to (underneath) the spray nozzle. To achieve an efficient wetting of the wall, operating the nozzles for the deposit preventing liquid at low pressure drop values is preferred. To this end, pressure drop values of from 0.1 bar to 5.0 bar, preferably of from 0.3 bar to 2.0 bar, most preferred of from 0.5 bar to 1.5 bar, are advantageously applied. It is furthermore preferred that the nozzle openings of the nozzles for the deposit preventing liquid should have, at a given pressure loss and volume flow of deposit preventing liquid, the largest possible diameter. Flat-jet nozzles are preferred as nozzles for the deposit preventing liquid. In contrast to the operation of the quenching zone, there is thus no spraying of the liquid directly into the gaseous reaction mixture. The film prevents the contact of the gaseous reaction mixture with the wall above the quenching zone and thereby inhibits formation of solid deposits.

The deposit preventing liquid injected to areas in the cross-sectional plane of the deposit preventing zone before the entrance to the quenching zone (i.e. in accordance with b)(ii)) can break loose the solid deposits formed above the entrance to the quenching zone by mechanical force. The deposit preventing liquid injected to the solid deposits formed above the entrance of the quenching zone will evaporate as it comes into contact with the relatively hot solid deposits, resulting in a cooling effect, causing thermal stress between inside and surface of the solid deposits, supporting breaking loose the solid deposits. The nozzles used in variant b)(ii) can be of the same type as those used in variant b)(i). Different nozzles may also be used, however. In this case, full-jet nozzles or flat-jet nozzles are preferred. Variant b)(ii) can be carried out during operation, i.e. during production of isocyanate, so as to delay shutdowns for maintenance. Variants b)(i) and b)(ii) can also be carried out simultaneously.

Thus, an advantage of the quenching process according to the present invention is that the formation of solid deposits above the quenching zone can be prevented efficiently and/or the solid deposits formed above the quenching zone can be removed efficiently.

The spray nozzles for the quenching liquid are preferably arranged at equal distances along the circumference of the entrance to the quenching zone.

Spraying of the quenching liquid is performed with conventional spray nozzles or via openings, such as slits or holes, at the entrance to the quenching zone. If only two spray nozzles are provided, these are preferably arranged diametrically opposite to each other. The spray nozzles may preferably be individual nozzles. More preferably, nozzle heads, each with at least two individual nozzles, are used, wherein single substance nozzles are preferably chosen.

Another advantage of the process according to the present invention is that the desired rapid cooling of the gaseous reaction mixture which contains a diisocyanate, hydrogen chloride and excess phosgene from 300° C. to 400° C. on leaving the reaction zone to a maximum of 200° C. on leaving the quenching zone is produced by the spraying of a suitable quenching liquid. The contact time during which cooling takes place is reduced to 0.2 s to 3 s.

Still another advantage of the process of the present invention is that the quenching liquid is sprayed into the gas stream in such a way that the hot reaction gas does not make contact with the relatively cold surfaces of the quenching zone or the spray nozzles for the quenching liquid and their pipes. Only after the gaseous reaction mixture has cooled to the stable temperature range for the particular diisocyanate does it come into contact with the relatively cold walls of the quenching zone or other components.

The spray nozzles for the quenching liquid are preferably arranged independently of each other in such a way that the direction of flow of each quenching liquid is preferably at an angle of 0° to 50°, more preferably 20° to 35°, to the direction of flow of the gas mixture. The direction of flow of the gas mixture is substantially along the axis of the cylindrical reaction zone or of the quenching zone. If the tubular reactor is arranged in an upright position, the gas flows from top to bottom through the reaction zone and the downstream quenching zone. In the same way, the direction of flow of the quenching liquid is along the axis of the spray nozzle for the quenching liquid. The cone angle of the spray nozzles, independently of each other, is preferably 20° to 90°, more preferably 30° to 60°. In one embodiment, the directions of flow of all those nozzles which are arranged in one plane have the same angle to the direction of flow of the gas mixture and the same cone angle. Hollow cone nozzles or full cone nozzles are preferred as nozzles for the quenching liquid.

The quenching liquid comprises an organic solvent or a mixture of different organic solvents which do not react with the diisocyanate formed. Suitable solvents can be selected from, for example, toluene, chlorobenzene, dichlorobenzene, chlorotoluene, xylene and chloronaphthalene. Dichlorobenzene includes para-dichlorobenzene and ortho-dichlorobenzene, and xylene includes para- xylene and ortho-xylene.

A solution of the diisocyanate formed in one of above organic solvents may also be used. In this case, the proportion of the solvent is preferably 10% to 99% by mass, preferably 40% 70% by mass, based on the total mass of the solution.

The temperature of the quenching liquid is from −20° C. to 200° C. Preferably, the temperature of the quenching liquid is from 100° C. to 170° C.

The quenching zone downstream of the cylindrical reaction zone is also preferably cylindrical. The diameter of the quenching zone may be chosen to be substantially identical to that of the reaction zone or larger than that of the reaction zone. The reaction zone is preferably a tubular reactor without baffles.

The process according to the present invention has the further advantage that cooling of the gaseous reaction mixture takes place rapidly, preferably within 0.2 s to 3 s, immediately after reaction has taken place, because the gas stream flowing out of the reactor does not have to be slowed down and/or passed into a container but is passed directly through a stream of an atomized quenching liquid. In addition, the quenching zone is designed in such a way and the nozzles are mounted in such a way that the hot gas mixture does not make contact with any of the relatively cold surfaces in the quenching zone. For this purpose, for example, the diameter of the cylindrical quenching zone may be larger than the diameter of the reaction zone.

In the following description, the process according to the present invention is illustrated in more detail making reference to the figures.

Figure 1:
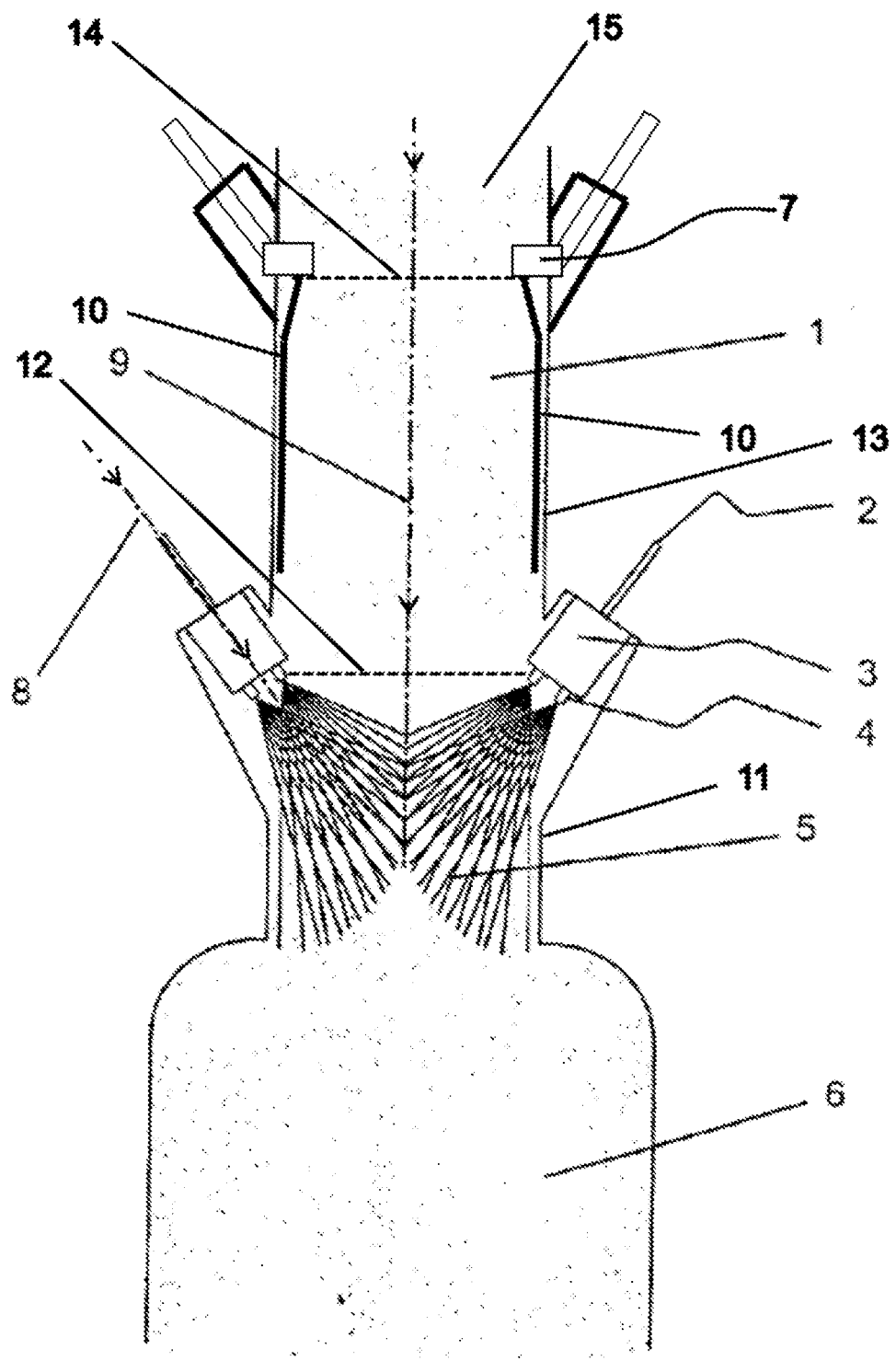
FIG. 1 shows a schematic diagram of an embodiment according to the present invention, wherein the process is conducted according to variant b)(i). The reference numerals have the following meanings.

FIG. 1 shows a cylindrical deposit preventing zone 1, through which the gaseous reaction mixture flows from top to bottom along the broken centerline 9. On leaving the deposit preventing zone 1, the gaseous reaction mixture flows through a similarly cylindrical quenching zone 5. At the entrance of the deposit preventing zone 1, there are twelve spray nozzles for the deposit preventing liquid 7 (only two of them are shown), which spray the deposit preventing liquid towards the wall of the deposit preventing zone to form a deposit preventing film 10. Each nozzle sprays the deposit preventing liquid to the part of the wall that is adjacent to (underneath) said nozzle. In the quenching zone, there are twelve nozzle heads 3 (only two of them are shown), each with several individual nozzles 4, located diametrically opposite to each other. The quenching liquid is supplied to nozzle head 3 via a pipe 2. Nozzles 4 and nozzle head 3 preferably are arranged such that the direction of flow of the quenching liquid (shown by broken centerline 8) and that of the gas stream 9 are at an angle of 0° to 50°, more preferably 20° to 35°, to each other and thus the hot gaseous reaction mixture does not make contact with the colder nozzles and nozzle heads. In the quenching zone 5, cooling of the gaseous reaction mixture takes place by evaporation of the atomized liquid. The remaining liquid and the cooled reaction gas pass into the liquid collection container 6 located below the quenching zone, this container acting simultaneously as a pump reservoir and as apparatus to separate gas and liquid.

The quenching zone of the embodiment shown in FIG. 2 corresponds in principle to that of the embodiment shown in FIG. 1. Identical or similar components therefore have the same reference numbers as in FIG. 1. The embodiment shown in FIG. 2 differs from that shown in FIG. 1 in that the deposit preventing liquid stream 10a from spray nozzles for the deposit preventing liquid 7 is sprayed towards solid deposits 16 deposited above the quenching zone.

In the present application, "the formation of solid deposits above the quenching zone can be prevented efficiently" means that no or very little solid deposits form above the quenching zone after a long period, for example one to several weeks of operation.

In the present application, "the solid deposits formed above the quenching zone can be removed efficiently" means that the solid deposits formed above the quenching zone are broken loose and peeled off so as not to block the passage for the gaseous reaction mixture.

In another aspect, the present invention relates to a process for preparing a diisocyanate by phosgenation of a diamine (i.e. the diamine corresponding to the diisocyanate), comprising the steps:

Providing a gaseous stream comprising the diamine and a gaseous stream comprising phosgene, Mixing the gaseous stream comprising the diamine and the gaseous stream comprising phosgene, and guiding the mixed gaseous streams through a reaction zone, thereby forming a gaseous reaction mixture comprising a diisocyanate, phosgene and hydrogen chloride, Quenching, in a quenching zone downstream of the reaction zone, the gaseous reaction mixture comprising a diisocyanate, phosgene and hydrogen chloride, the process further comprising:

(a) injecting a quenching liquid in the quenching zone by passing the quenching liquid through spray nozzles for the quenching liquid arranged at the entrance to the quenching zone, thereby partially condensing the gaseous reaction mixture; and (b) injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, and/or (ii) to areas in a cross-sectional plane of the deposit preventing zone before the entrance to the quenching zone.

It goes without saying that all embodiments described above of the process for quenching a gaseous reaction mixture that is obtained in a reaction zone upstream of the quenching zone by phosgenation of a diamine in the gas phase can be applied to this process for preparing a diisocyanate by phosgenation of a diamine.

The desired diisocyanate is largely to completely condensed in the quenching zone and isolated from the resulting liquid reaction mixture leaving the quenching zone, preferably by distillation. The gaseous phase leaving the quenching zone comprises excess phosgene and hydrogen chloride.

EXAMPLES

Example 1 (Inventive)

Toluene diamine and phosgene were fed into a vertically arranged gas phase phosgenation tubular reactor with a diameter of about 2 meters and a height of about 20 meters at 12.5 t/h toluene diamine (TDA) vapours and 62 t/h phosgene, respectively. A gaseous reaction mixture comprising toluene diisocyanate (TDI), hydrogen chloride and excess phosgene at about 400° C., at a pressure of 1600 mbar left the tubular reactor at a flow rate of 74.5 t/h and entered the downstream deposit preventing zone and the quenching zone both with a diameter of about 2 meters at a velocity of about 5 m/s.

A deposit preventing liquid comprising 95% by mass of ortho-dichlorobenzene (ODB) and 4% by mass of toluene diisocyanate (the % by mass is based on the total mass of the deposit preventing liquid) was continuously supplied to a ring of 12 spray nozzles for the deposit preventing liquid arranged at the entrance of the deposit preventing zone with a height of 1.8 meter of the gas phase phosgenation reactor at a flow rate of 68 m$^3$/h, and flowing down along the wall of the deposit preventing zone through the spray nozzles for the deposit preventing liquid. The temperature of the deposit preventing liquid was 158° C.

A quenching liquid comprising 50% by mass of ortho-dichlorobenzene and 45% by mass of toluene diisocyanate (the % by mass is based on the total mass of the quenching liquid) was supplied continuously to spray nozzles for the quenching liquid of the Gas Phase Phosgenation reactor at a flow rate of 360 m$^3$/h. The temperature of the quenching liquid was 151° C.

The quenching liquid was pumped and supplied continuously to 12 spray nozzles for the quenching liquid arranged at equal distances along the circumference of the entrance of the quenching zone. The quenching liquid was atomized and sprayed into the gaseous reaction mixture through the spray nozzles for the quenching liquid for cooling the gaseous reaction mixture. When passing the quenching zone, the temperature of the hot reaction gas decreased from about 400° C. to 200° C., resulting in condensation of most of toluene diisocyanate.

With injection of the deposit preventing liquid, the formation of solid deposits resulting in significant reaction gas pressure loss over the quenching zone can be prevented effectively. After 78 days of operation, only a small ring of solid deposits could be observed above the spray nozzles for the quenching liquid, while no solid deposit could be observed underneath the spray nozzles for the quenching liquid. During the whole operation of 78 days, no differential pressure spikes due to quenching could be observed.

Example 2 (Comparative)

Toluene diamine and phosgene were fed into a vertically arranged gas phase phosgenation tubular reactor with a diameter of about 2 meters and a height of about 20 meters at 12.5 t/h toluene diamine (TDA) vapors and 62 t/h phosgene, respectively. A gaseous reaction mixture comprising toluene diisocyanate (TDI), hydrogen chloride and excess phosgene at about 400° C., at a pressure of 1600 mbar left the tubular reactor at a flow rate of 74.5 t/h and entered the downstream quenching zone with a diameter of about 2 meters at a velocity of about 5 m/s.

A quenching liquid comprising 50% by mass of ortho-dichlorobenzene and 45% by mass of toluene diisocyanate (the % by mass is based on the total mass of the quenching liquid) was supplied continuously to spray nozzles for the quenching liquid of the gas phase phosgenation reactor at a flow rate of 360 m³/h. The temperature of the quenching liquid was 151° C.

The quenching liquid was pumped and supplied continuously to 12 spray nozzles for the quenching liquid arranged at equal distances along the circumference of the entrance of the quenching zone. The quenching liquid was atomized and sprayed into the gaseous reaction mixture through the spray nozzles for the quenching liquid for cooling the gaseous reaction mixture. When passing the quenching zone, the temperature of the hot reaction gas decreased from about 400° C. to 200° C., resulting in condensation of most of toluene diisocyanate.

After 61 days of operation, a large amount of solid deposits was observed above the spray nozzles for the quenching liquid, and the solid deposits almost closed the entire passage of the reactor, causing significant reaction gas pressure loss that eventually forced the reactor to get shut down. During the continuous operation of 61 days, several differential pressure spikes up to 100 mbar could be observed.

The invention claimed is:

1. A process for quenching, in a quenching zone, a gaseous reaction mixture comprising a diisocyanate, phosgene and hydrogen chloride that is obtained in a reaction zone upstream of the quenching zone by phosgenation of a diamine in the gas phase, the process comprising:
   (a) injecting a quenching liquid in the quenching zone by passing the quenching liquid through spray nozzles for the quenching liquid arranged at the entrance to the quenching zone, thereby partially condensing the gaseous reaction mixture; and
   (b) injecting a deposit preventing liquid in a deposit preventing zone located between the reaction zone and the quenching zone by passing the deposit preventing liquid through spray nozzles for the deposit preventing liquid arranged at the entrance to the deposit preventing zone above the spray nozzles for the quenching liquid, wherein each spray nozzle for the deposit preventing liquid sprays the deposit preventing liquid (1) onto a wall segment of the deposit preventing zone that is adjacent to said spray nozzle for the deposit preventing liquid to produce a film of the deposit preventing liquid flowing along the wall, and/or (ii) to areas in a cross-sectional plane of the deposit preventing zone before the entrance to the quenching zone.

2. The process according to claim 1, wherein the deposit preventing zone has a height in the range of 1.5 centimeters to 5 meters.

3. The process according to claim 1, wherein the spray nozzles through which the deposit preventing liquid is passed are arranged at equal distances along the circumference of the entrance of the deposit preventing zone.

4. The process according to claim 1, wherein the spray nozzles through which the quenching liquid is passed are arranged at equal distances along the circumference of the entrance of the quenching zone.

5. The process according to claim 1, wherein the process comprises injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, and (ii) to areas in a cross-sectional plane of the deposit preventing zone before the entrance to the quenching zone.

6. The process according to claim 1, wherein the process comprises injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (i) onto a wall segment of the deposit preventing zone that is adjacent to said spray nozzle for the deposit preventing liquid to produce a film of the deposit preventing liquid flowing along the wall, but not (ii) to areas in a cross-sectional plane of the deposit preventing zone before the entrance to the quenching zone.

7. The process according to claim 1, wherein the process comprises injecting a deposit preventing liquid in a deposit preventing zone located between the reaction zone and the quenching zone by passing the deposit preventing liquid through spray nozzles for the deposit preventing liquid at the entrance to the deposit preventing zone, wherein each spray nozzle for the deposit preventing liquid sprays the deposit preventing liquid (ii) to areas in a cross-sectional plane of the deposit preventing zone before the entrance to the quenching zone, but not (i) onto a wall segment of the deposit preventing zone that is adjacent to said spray nozzle for the deposit preventing liquid to produce a film of the deposit preventing liquid flowing along the wall.

8. The process according to claim 1, wherein the deposit preventing liquid is a solvent or a mixture of different solvents comprising toluene, chlorobenzene, chlorotoluene, dichlorobenzene, xylene or chloronaphthalene.

9. The process according to claim 1, wherein the deposit preventing liquid is a solution of the product diisocyanate dissolved in a solvent or a mixture of different solvents comprising toluene, chlorobenzene, chlorotoluene, dichlorobenzene, xylene or chloronaphthalene, wherein the solvent or mixture of solvents represents 40% to 99% by mass, based on the total mass of the solution.

10. The process according to claim 1, wherein the temperature of the deposit preventing liquid is −20° C. to 200° C.

11. The process according to claim 1, wherein the quenching liquid is a solvent or a mixture of different solvents comprising toluene, chlorobenzene, chlorotoluene, dichlorobenzene, xylene or chloronaphthalene.

12. The process according to claim 1, wherein the quenching liquid is a solution of the product diisocyanate dissolved in a solvent or a mixture of different solvents comprising toluene, chlorobenzene, chlorotoluene, dichlorobenzene, xylene or chloronaphthalene, wherein the solvent or mixture of different solvents represents 10% to 99% by mass, based on the total mass of the solution.

13. The process according to claim 1, wherein the temperature of the quenching liquid is −20° C. to 200° C.

14. The process according to claim 1, wherein the process for quenching the gaseous reaction mixture is part of a process for preparing a diisocyanate by phosgenation of a diamine comprising:

providing a gaseous stream comprising the diamine and a gaseous stream comprising phosgene, and mixing the gaseous stream comprising the diamine and the gaseous stream comprising phosgene, and guiding the mixed gaseous streams through the reaction zone, thereby forming the gaseous reaction mixture comprising a diisocyanate, phosgene and hydrogen chloride.

15. The process according to claim 14, wherein the diisocyanate is isolated from the condensed reaction mixture leaving the quenching zone by distillation.

* * * * *